US010078042B2

(12) United States Patent
Poiate Junior et al.

(10) Patent No.: US 10,078,042 B2
(45) Date of Patent: Sep. 18, 2018

(54) METHOD FOR TESTING NON-UNIFORM LOADS IN PIPES

(75) Inventors: Edgard Poiate Junior, Sao Paulo (BR); Jose Nunes Pimentel Neto, Macae (BR); Fernando Antonio Santos Medeiros, Niteroi (BR); Alvaro Maia Da Costa, Niteroi (BR); Jose Luiz Falcão, Niteroi (BR); Claudio Dos Santos Amaral, Rio de Janeiro (BR); Renato Seixas Da Rocha, Rio de Janeiro (BR)

(73) Assignee: PETRÓLEO BRASILEIRO S.A.—PETROBRAS, Rio de Janeiro (BR)

(*) Notice: Subject to any disclaimer, the term of this patent is extended or adjusted under 35 U.S.C. 154(b) by 431 days.

(21) Appl. No.: 14/360,830

(22) PCT Filed: Dec. 22, 2011

(86) PCT No.: PCT/BR2011/000488
§ 371 (c)(1),
(2), (4) Date: May 27, 2014

(87) PCT Pub. No.: WO2013/091034
PCT Pub. Date: Jun. 27, 2013

(65) Prior Publication Data
US 2015/0101397 A1    Apr. 16, 2015

(51) Int. Cl.
*G01N 3/12* (2006.01)
*E21B 47/00* (2012.01)
(Continued)

(52) U.S. Cl.
CPC ........... *G01N 3/12* (2013.01); *E21B 47/0006* (2013.01); *E21B 49/003* (2013.01);
(Continued)

(58) Field of Classification Search
CPC ................................ G01N 3/12; E21B 49/003
See application file for complete search history.

(56) References Cited

U.S. PATENT DOCUMENTS 5,284,207 A * 2/1994 Bittleston .............. C09K 8/528
166/285
5,529,735 A * 6/1996 Durham ................ B28B 11/006
264/154

(Continued)

FOREIGN PATENT DOCUMENTS

WO    2011/122955 A1    10/2011

OTHER PUBLICATIONS

International Search Report of PCT/BR2011/000488, dated Mar. 1, 2012.

*Primary Examiner* — Daniel S Larkin
*Assistant Examiner* — Alexander Mercado
(74) *Attorney, Agent, or Firm* — Sughrue Mion, PLLC

(57) ABSTRACT

The present invention refers to a method wherein a test body is assembled in specific configurations to be submitted to testing in a conventional hydrostatic chamber. The method calls for assembling a test body that simulates cementing failures, the presence of stress anisotropy and a borehole of irregular geometry, by pressurizing said test body in a conventional hydrostatic chamber. The uniform forces are distributed circumferentially around a casing stream in a non-uniform way, simulating operating conditions that are as close as possible to reality, enabling an analysis of how the structure reacts in scenarios similar to actual conditions.

17 Claims, 5 Drawing Sheets

(51) Int. Cl.
*E21B 49/00* (2006.01)
*G01M 5/00* (2006.01)

(52) U.S. Cl.
CPC ... *G01M 5/0058* (2013.01); *G01N 2203/0042* (2013.01); *G01N 2203/0246* (2013.01); *G01N 2203/0274* (2013.01)

(56) References Cited

U.S. PATENT DOCUMENTS

| | | |
|---|---|---|
| 7,051,600 B1 | 5/2006 | Cavallaro et al. |
| 7,669,482 B2 | 3/2010 | Jacobs et al. |
| 7,757,775 B2 | 7/2010 | Hammami et al. |
| 2008/0034885 A1 | 2/2008 | Monteiro et al. |
| 2008/0164022 A1 | 7/2008 | Jacobs et al. |
| 2010/0077691 A1* | 4/2010 | Constantz ............... C04B 22/10 52/596 |

* cited by examiner

METHOD FOR TESTING NON-UNIFORM LOADS IN PIPES

FIELD OF THE INVENTION

The present invention refers to a method for testing pipes to be submitted to non-uniform loads. Said method includes the preparation of segments of casing strings used in oil fields, for testing using conventional hydrostatic chambers.

The method enables the application of non-uniform circumferential loads, simulating operating conditions that are as close as possible to reality, providing an analysis of how the test structure would react in scenarios similar to actual operating conditions.

BACKGROUND OF THE INVENTION

At the end of each step of drilling a well, whether in an onshore or offshore field, a casing string must be placed in the borehole and pass through successive geological layers, comprised of the various types of rock formed over thousands of years and different environmental conditions and geological processes. Thus, they may have different mineralogical compositions, geomechanical properties and field orientations/stresses.

A borehole will receive successive columns during the course of its lifetime, placed during the different steps of the well drilling process, until the crude oil reservoir to be explored is reached. These retain a cylindrical cross-section for a certain period of time. However, as the borehole penetrates successive lithological layers of differing geomechanical properties and different stresses, the walls of the column within each section may be deformed, losing their original circular cross-section, or the column axis may be displaced relative to the columns in the sections immediately above or below it.

It is common knowledge that the oil industry has operated in ultra-deep salt layers. A marked characteristic of this mineral is its remarkable ability to creep and slowly deform under steady-state variables over a short period of time, even under low stress and temperature conditions.

From the point of view of exploration, the presence of salt rocks in hydrocarbon prospects increases the likelihood of success, as these sediments may deform and create diverse structures that favor the accumulation of hydrocarbons. Furthermore, they are practically impermeable and thus make good cappers.

However, when it comes to drilling oil wells, compared to other lithologies, the presence of salt rock is associated with additional problems due to creep.

This physical phenomenon is measurably influenced by deviatoric stresses, the absolute temperature and the type of salt. The greater the depth and thickness of the layer of salt rock that must be drilled through, the greater will be the deviatoric stress and the temperature, and thus it is more likely that the borehole will close over time.

Typical consequences one can anticipate range from restricting the passage of the drilling column, to irreversible entrapment requiring a change in the course of the borehole or even abandoning the well altogether. However, over the medium and long term, salt creep also places additional loads on the casing strings, and may cause ovalisation, thus limiting the passage of the tools required to for well completion and production.

Depending on the degree of ovalisation of the casing string, it can become impossible to remove the production equipment from within the well (installed within the casing string), or it can become damaged, resulting diminished or even no production from the well. Depending on the situation of a given borehole, salt creep can stress the casing string in unexpected directions, and can even result in rupture or collapse of the string if it was not properly sized.

Thus the lifetime of the well, which is designed to last for 20 to 30 years, is drastically reduced under such a severe scenario, subject to unexpected stresses. Oftentimes this requires building a new, unplanned borehole that was not included in the budget to develop the oilfield.

Thus salt creep must be taken into consideration over the entire lifetime of the well as a function of the casing used and the conditions for building and operating the well; one must especially take into consideration a number of events and conditions that may occur during the lifetime of the well, changing the stresses and the temperature to which it is subject.

For example, the start of production increases the temperature along the length of the well, while maintenance operations may result in decreased pressure inside the pipe, both of which may be detrimental to pipe integrity, given the increase in the creep rate of the evaporite rock surrounding the borehole, and a reduction of the internal reaction force the pipe exerts on the salt layer.

Injecting hot steam into boreholes, a process that is routinely used to recover crude oil, and the resulting corrosion of the coating wall, are further unfavorable events, similar to those mentioned in the previous paragraph, and that also play an important role in the structural integrity of pipe.

Numerous authors have studied the resistance to failure of casing strings subject to different non-uniform load conditions, compared to their resistance when submitted to hydrostatic loads according to specifications published by the American Petroleum Institute (API).

These studies were motivated by the failure of casing strings in salt layers, detected a few weeks to a few years after they had been installed in oil wells. It is assumed that failures are the result of non-uniform loads placed on the casing due to incomplete cementing of borehole with enlarged boreholes (extra borehole caliper), as seen in consecutive borehole profiles.

On the other hand, it has been found almost empirically that in some cases, in order to offer the same resistance to collapse, casings submitted to non-uniform loads must have wall thicknesses 3 or 4 times the wall thickness of casings submitted to hydrostatic loads.

As the creep of evaporite rocks is substantially influenced by temperature and stress, the deeper the layer of the evaporitic rock to be traversed by the borehole, the greater will be the deviatoric stresses and temperature acting on the well.

However, because of the different chemical composition and microstructures that characterize the diverse types of evaporite created by nature, they are expected to present different creep behaviors when submitted to the same boundary conditions. For this reason, the load placed on casing strings due to salt creep can vary widely with borehole depth.

In general, boreholes containing regions that are whorled or with extra borehole caliper (widened), whether or not these are associated with off-center borehole casings, may not enable suitable cleaning of the borehole wall liner, resulting in gaps in the cementing paste (channeling), resulting in poor cementing of this region and the one above it. Consequently, the coating may be subjected to non-uniform and spot loads; these conditions are not among the criteria used to calculate the collapse performance of coatings in API 5CT (ISO 11960), which is based on uniformly distributed radial loads.

Resistance to collapse in pipes is a complex combination of a number of variables: geometric characteristics, the properties of the metal the pipe is built of, the loads applied and the means used to secure the pipe.

Among the geometric factors, we have the internal pipe diameter, wall thickness, ovalisation, eccentricity and variations in pipe thickness.

Among the mechanical properties of the material, we have yield stress, elasticity module, the shape of the stress-strain curve and residual stresses.

The loads applied may be associated with an external load acting circumferentially to other loads such as axial compression and traction, bending, torsion and internal pressures.

Regarding how pipes are fixed, we have the length of free (non-secured) pipe that is subject to the forces, and the contact area with rock.

However, testing equipment currently available to determine the collapse load of pipe enables assembling only a section of pipe in a chamber, which is then submitted to increasing hydrostatic loads for a period of time until collapsing.

Collapse pressure is calculated using analytical equations specified in API 5CT (ISO 11960), which are based on uniformly distributed radial loads.

Thus, currently available hydrostatic chambers present shortcomings, especially as they put only hydrostatic pressure on the pipe, which is not representative of the phenomena that may actually take place in salt zones and in regions with stress anisotropy.

Although it is possible, using currently available digital technology and computational modeling, to create mathematical models that simulate the various non-uniform forces, and use these virtual models to define sufficient data parameters to design casing strings under different boundary conditions, this data cannot be proven using the currently available hydrostatic chambers.

Documents US 2008/0034885 A1 and U.S. Pat. No. 7,051,600 show some examples of equipment capable of submitting a structure to multiple forces, however this equipment is not sufficient to generate simultaneous and non-uniform forces along a structure, and are thus unable to validate the values obtained from using numerical modeling.

Document U.S. Pat. No. 7,669,482 describes equipment capable of applying loads, displacements, temperature and pressure on pipes to simulate the conditions at the bottom of a well. However, in addition to being a large and expensive piece of equipment, the description contains none of the internal details of the apparatus.

Document BR 020100121966 of 30 Dec. 2010, by the same depositor, shows equipment with components suitably built to submit a structure to multiple, non-uniform efforts simultaneously, and thus suitable for validating the values obtained using the numerical modeling in question with a large degree of precision. However, this too is a large and expensive device built to deliver great performance and focused on testing any longilinear structure, not only to simulate the results of cementing failures, but also for numerous other simulations such as creep, buckling and torsion, among others.

Thus, although there exists suitable technology for submitting a structure to non-uniform loads that can validate the values obtained from numerical models, the continuous search for savings and to use the resources available at industrial facilities has led to research into new techniques.

In light of this technical challenge, there emerged a concern with developing a method capable of using technological resources already available, so as to deploy them to validate the results obtained from computer models that are as close as possible of the actual situation found in structures designed for oil wells.

Thus, research has focused especially on using the largest and most conventional test equipment available right now for oil well casing strings: hydrostatic chambers.

It is known that the currently available hydrostatic test chambers are capable of submitting oil well casing strings to homogeneous loads only, and to date there have been no techniques for using this load analysis device in such a way as to provide the means to simulate loads applied in a non-uniform manner along the length of oil well casing strings. The object of the invention described herein is to structure a method to apply non-uniform loads to structures using a conventional hydrostatic chamber.

Other objectives the present invention proposes to reach are:
 a) enable the application of non-uniform loads to a structure;
 b) reduce casing string failure rate;
 c) enable conducting tests that are as close as possible to the actual situation under which the structures designed for oil wells will operate;
 d) ensure certification of the structural integrity of the borehole built.

SUMMARY OF THE INVENTION

The present invention refers to a method for testing non-uniform loads applied to pipes using conventional hydrostatic test chambers, with a test body mounted under specific conditions.

This method expects to collect a body of evidence that simulates non-uniform loads resulting from cementing failures or borehole of irregular (non-cylindrical) geometry. The test body is obtained from two pipes, placed one inside the other and flanged to each other so as to create a chamber between the outer surface of the inner pipe and the inner surface of the outer pipe, said chamber being suitable for filling with cement interspersed with previously determined empty spaces. The inner pipe represents a section of the casing string placed within a containment pipe, and the empty portions are meant to simulate cementing failures.

The empty spaces may optionally be provided with a means of access through the casing string, through which pressure can be placed using, for example, an air compressor or regular pump.

The test body is fitted with semi-spherical flanges at both ends, and with an access means that enables pressure to be applied inside the casing string using an air compressor or pump.

The test body is shaped according to the specific criteria under which one desires to run the test, placed in a conventional hydrostatic chamber, and the chamber pressurized. Uniform stresses generated by the hydrostatic chamber, together with the action of the compressors capable of changing the pressure in the areas that simulate failures and inside the casing string reproduce a controlled scenario of non-uniform loads (N) applied to the casing string under analysis. Deformations are measured using sensors inserted into the pipe itself.

BRIEF DESCRIPTION OF THE DRAWINGS

A more particular description of the invention is provided below, together with the drawings listed below, presented herein merely as examples and form an integral part of this report.

DETAILED DESCRIPTION OF THE INVENTION

This invention provides an innovative method for testing oil well casing pipes by applying non-uniform loads artificially generated inside conventional hydrostatic chambers.

The basic principle of the method, the focus of which reveals the means required to achieve a realistic testing scenario, is sufficient so that those skilled in the art will immediately realize that small changes may be applied to generate methodological variations or mode using the same conventional equipment used.

This invention provides the means to use existing equipment to validate the outcome of numerical simulations of the integrity of borehole to be built in salt zones or in areas with stress anisotropy obtained through digital processing, as the criteria (testing, equipment, etc.) determined by American Petroleum Institute (API) standards do not provide for loads generated in a non-uniform manner.

By using the proposed method to validate the numerical simulations, the industry will have a further means it can use to quantify casing strings installed in salt zones or in areas of stress anisotropy using technical resources already available, which will also enable reducing the cost and risk associated with building and operating oil wells.

Figure 1:
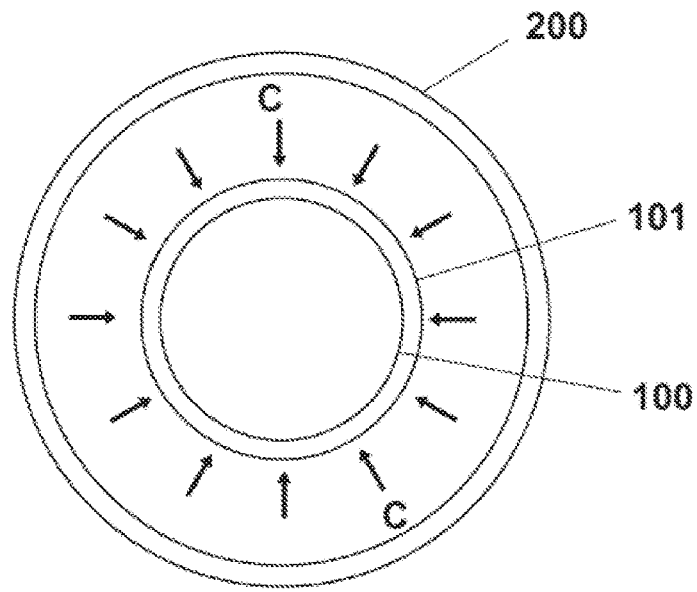
FIG. 1 shows a section of casing string inside the hydrostatic chamber during a traditional stress and strain analysis.
Figure 2:
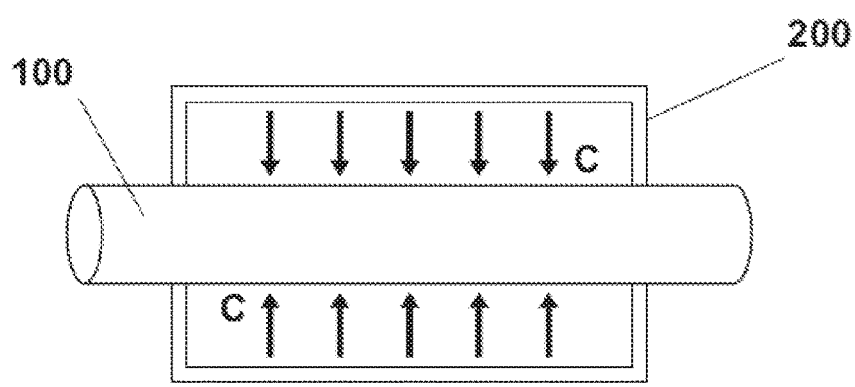
FIG. 2 shows a longitudinal cross-section of the casing string inside a conventional hydrostatic chamber.

In order to understand the object of this invention, which is methodology for testing pipes by applying non-uniform loads in conventional hydrostatic chambers, one must first look at FIG. 1 and FIG. 2 that show some of the basic details of the methodology available in PRIOR ART in conventional hydrostatic chambers available to the industry.

FIG. 1 is a cross-section of a casing string (100) within a hydrostatic chamber (200) submitted to compressive forces (C) along the outer surface (101) during a traditional stress and strain analysis.

FIG. 2 shows a longitudinal cross-section of the same casing string (100) inside a hydrostatic chamber (200), showing that the inside of the casing string (100) remains at atmospheric pressure when the load is uniformly distributed along the perimeter and the length of the casing string. In other words, this is an API condition found in cylindrical boreholes with pipes placed in the center of the borehole and no cementing gaps. Consequently, the equipment and methods used simulate a borehole built under ideal conditions, or in other words, a circular borehole with a perfectly centered casing string, with perfect cementing and located in an isotropic region. Under these conditions, for boreholes located in salt zones, the loads due to salt creep should be uniformly distributed along the perimeter of the casing, which is the API condition, which reduces the likelihood that the pipe will collapse.

Figure 3:
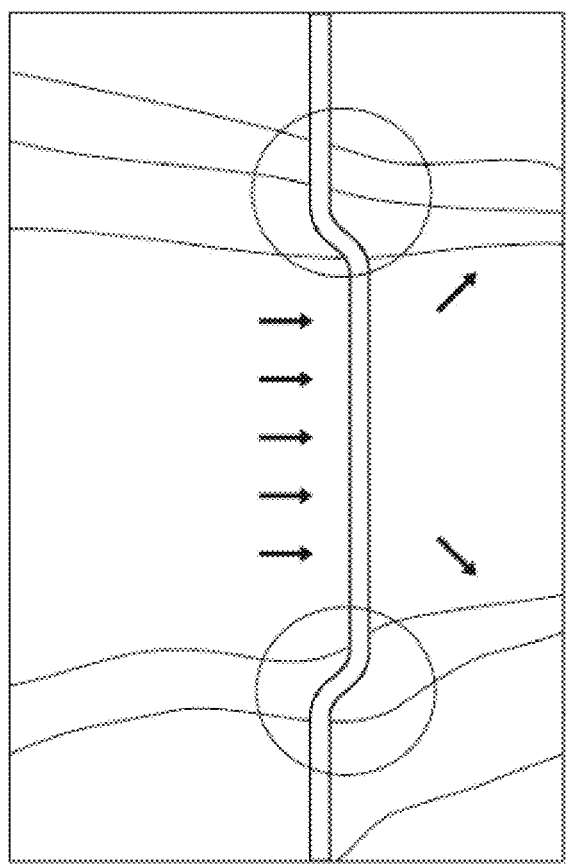
FIG. 3 is a diagram that exemplifies the conditions in an oil-well installed in a geomorphology known as canopy or salt-tongue.

FIG. 3 is a drawing of the cross-section of a geomorphology known as a typical salt-tongue or canopy, and the conditions for a borehole drilled into such a location. Creep of the surrounding geology and the conditions under which the borehole was built threaten its integrity.

Figure 4:
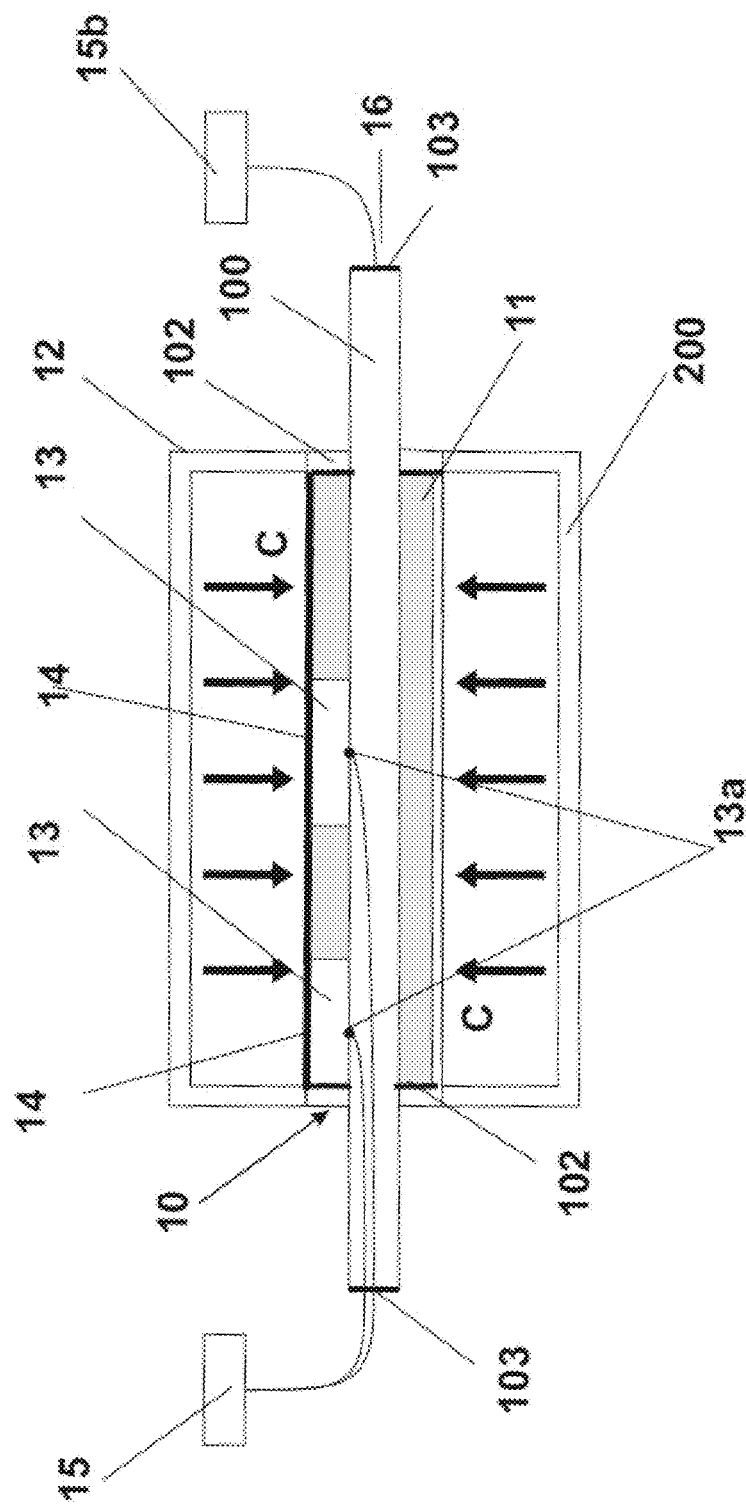
FIG. 4 is a schematic diagram of the invention showing a longitudinal cross-section of a conventional hydrostatic chamber being used with a test body mounted according to the proposed method.

FIG. 4 is a schematic representation of the invention, showing a longitudinal cross-section of a conventional hydrostatic chamber (200) used with a test body (10) mounted inside the chamber according to the proposed method, which includes preparing segments of the casing string (100) for testing the action of non-uniform loads due to situation such as cementing failures, stress anisotropy and irregular borehole geometry.

Figure 5:
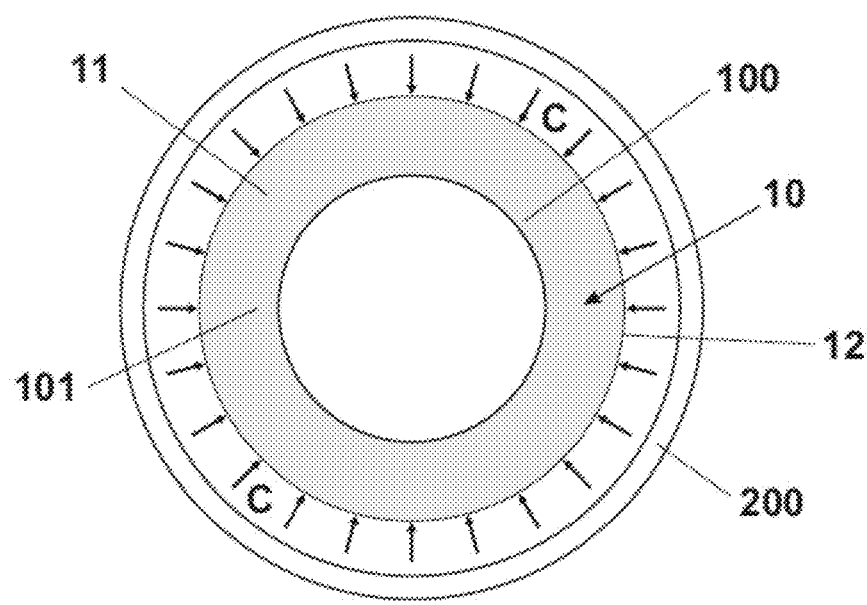
FIG. 5 is a cross-section of a conventional hydrostatic chamber with a test body simulating a well built under ideal conditions.
Figure 6:
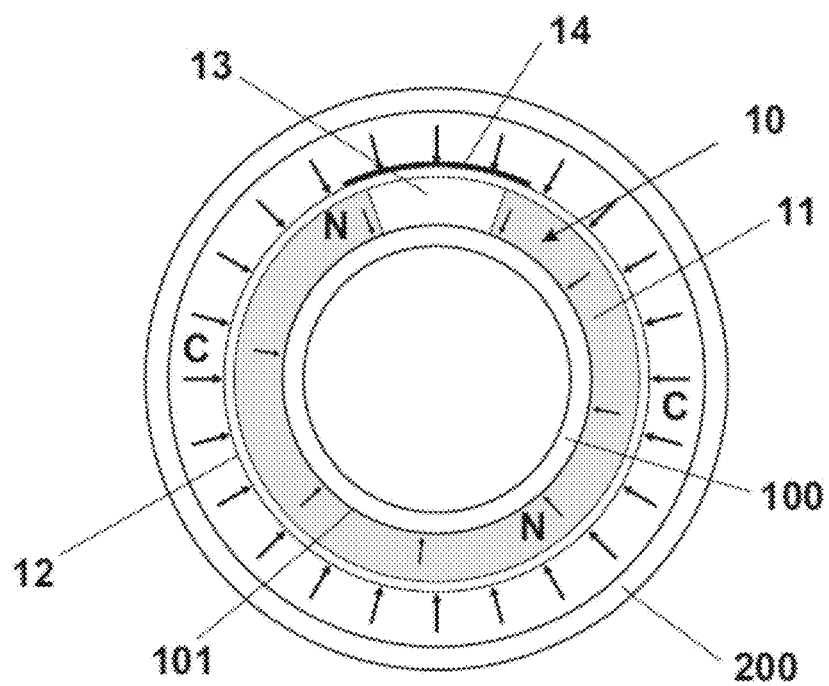
FIG. 6 is a cross-section of a conventional hydrostatic chamber with a test body simulating a well built under non-uniform load conditions.

The description of the proposed method may be followed in FIG. 4, together with FIGS. 5 and 6, which shows a cross-section of the test body (10) prepared according to the preferred assembly disposition.

In large part, the method consists of preparing the test body (10).

In order to achieve conditions of non-uniform loads, the test body (10) must be prepared from a basic assembly that simulates the scenario of an oil well and its components.

FIG. 5 shows a cross-section of a conventional hydrostatic chamber (200) with the casing string (100) to be tested, in which a test body (10) is used that simulates a borehole built under ideal conditions, or in other words, a circular borehole with a casing string (100) that is perfectly centered in the borehole and 100% cemented along the entire perimeter.

The test assembly for this simulation is comprised of a conventional hydrostatic chamber (200) containing said test body (10), comprised of a section of a casing string (100) surrounded by the cementing material (11) commonly used, which in turn is supported by a containment tube (12). Under these conditions, the load is uniformly distributed along the perimeter of the test body (10) and consequently the casing string (100).

One can easily see that a test body (10) may be obtained from two pipes that may or may not be concentric, flanged (102) to each other so as to create a chamber between the outer surface (101) of the inner pipe inner surface of an outer pipe, said chamber being suitable for holding a filling of cement until it is cured.

Once again, this reproduces API conditions, even in the presence of a layer of cement (11) between the point where the compression forces (C), exerted by the fluid inside the conventional hydrostatic chamber (200), act on the containment tube (12), and the surface of the casing string (100).

The load, represented by compression forces (C), is evenly transferred from the surface of the containment tube (12) to the cementing layer (11), and from there to the outer surface (101) of the casing string (100). To achieve this, it is important that the containment tube (12) be built of thin, not very resistant metal, acting merely as an element to support the cementing layer (11) of the test body (10).

Based on this basic assembly of the test body (10), the method proposes to assemble specific configurations of the test body (10) to simulate non-uniform loads, which can be created by situations such as cementing failures, stress anisotropy, and irregular borehole geometry.

FIG. 6 shows a cross-section of said conventional hydrostatic chamber (200) with the casing string (100) to be tested, in which a test body (10) is used to simulate a borehole built under non-uniform load conditions due to any of the situations described above: a circular or ovalised borehole with a casing string (100) that may or may not be centralized in the borehole, with high or low quality cementing along the entire perimeter, or with gaps in the cementing.

The test body (10) is prepared with a casing string (100) placed inside the containment tube (12), but not necessarily centralized in respect of the containment tube (12). One must also consider the possibility of providing an ovalised containment tube (12) to simulate a possible scenario where the borehole is elliptical.

The chamber that is created between the two pipes has at least one previously determined empty portion (13), obtained by using a balloon filled with air or fluid, or any other filler that is not representative for load transfer purposes, such as polyurethane, polyethylene or polystyrene foam, composites and even frames made of metal, wood, bamboo or other material.

Figure 7:
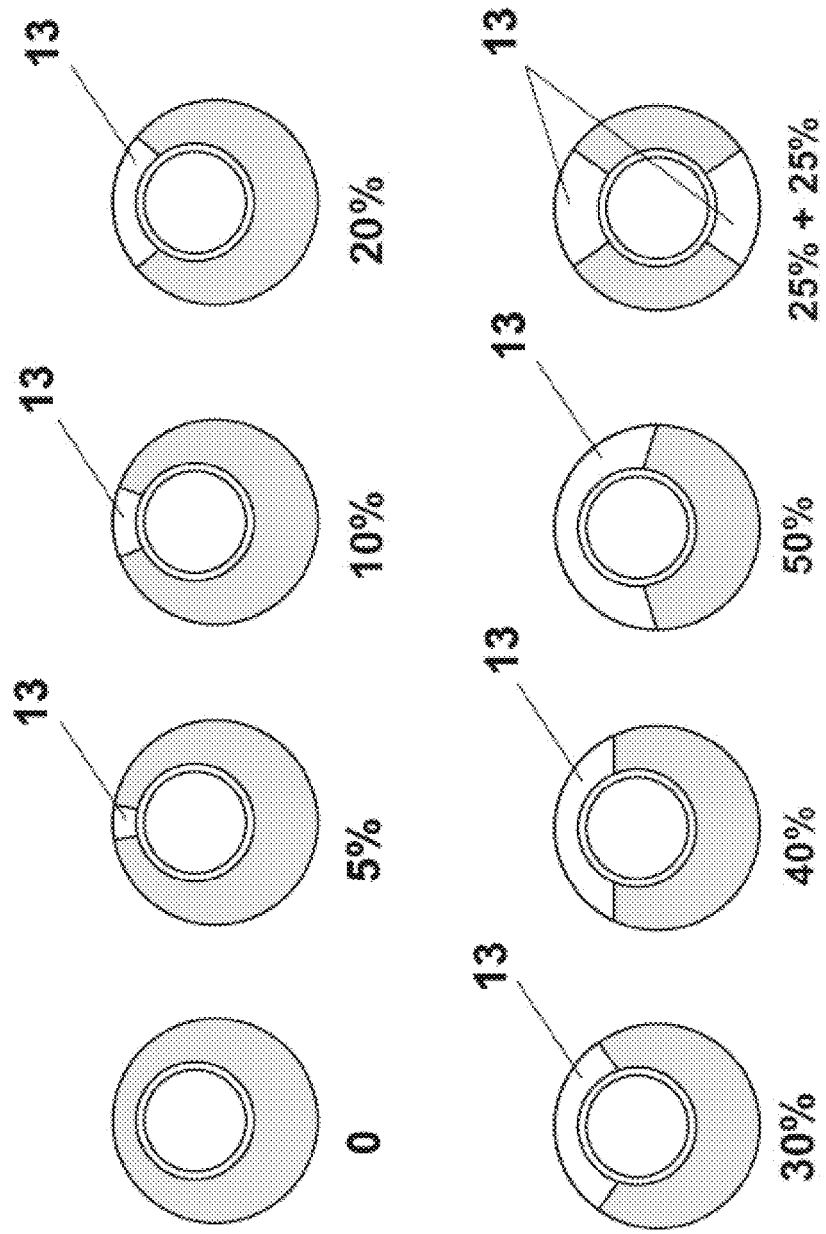
FIG. 7 shows some examples of simulated cementing failures in the form of empty spaces seen in the cross-section.

The empty portion (13) may represent from 1% to 100% of the total perimeter of the casing string (100), concentrated in a particular segment of the pipe or in segments distributed along the perimeter in a symmetrical or non-symmetrical way. FIG. 7 shows examples of cementing failure in the form of empty portions (13) forming a percent of the perimeter of the casing string (100). As shown in FIG. 6, the quality of the cementing in specific regions of the rest of the cemented chamber may also be altered in a controlled manner by changing the percentages of the components, the porosity, etc.

The containment tube (12) can be made of nonstructural metal. Where there are spaces (13) it is fitted with a piece of welded rolled sheet (14) as reinforcement so that the pipe does not burst during testing.

Going back to FIG. 4, we see that one or more of the empty spaces (13) have been optionally provided with a means of access (13a) through the casing string (100) to enable pressure to be applied to this region during testing, using either air or a fluid. The pressure may be changed using an air compressor or regular pump (15).

The test body (10) is also fitted with semi-spherical flanges (103) at both ends, or with an access means (16) that enables pressure to be applied inside the casing string (100) using an air compressor or pump (15b).

Once the test body (10) has been shaped according to the proposed method and within the specific criteria desired for testing, all one needs to do is place it in the conventional hydrostatic chamber (200) and start running the test.

The load, represented by the compression forces (C), is transferred from the surface of the containment tube (12) to the cement layer (11), and from there unevenly to the outer surface (101) of the casing column (100), resulting in a controlled and non-uniform pattern of loads on the pipe to be tested, which represents the casing string (100).

The uniform stresses generated by the hydrostatic chamber (200), together with the pressure generated by the compressors (15) and (15b), are capable of changing the pressure in the areas that simulate failures and inside the casing string, reproducing a controlled scenario of non-uniform forces (N) acting on the casing string (100) under analysis. Sensors are placed in the pipe to measure displacement and strain.

The method described herein thus demonstrates it is capable of precisely distributing the location and intensity of the loads placed on the test structure in a non-uniform manner, and is suitable for control and analysis.

The new method for testing non-uniform loads placed on pipes using conventional hydrostatic chambers may also be applied to the study of the effects created by salt rock creep on casing strings.

The invention is described herein with reference made to its preferred embodiments. It should be clear however, that this invention is not limited to these embodiments, and those skilled in the art will immediately realize that changes and substitutions are possible within the concept of invention described herein.

The invention claimed is:

1. A method for testing non-uniform loads on pipes, which employs a hydrostatic chamber provided with a test body, the method comprising:
   assembling the test body by placing an inner tube inside an outer tube;
   filling a cement layer between an outer surface of the inner tube and an inner surface of the outer tube, the cement layer including at least one empty space along a circumferential direction of the cement layer, the empty space being generated to represent cementing layer failures between a case string and a containment pipe;
   placing said test body in the hydrostatic chamber and pressurizing said hydrostatic chamber;
   applying uniform stresses on the outer tube along an axial direction of the outer tube and a circumferential direction of the outer tube, the uniform stresses being generated by the hydrostatic chamber; and
   measuring displacement and strain using sensor elements placed in the test body,
   wherein the empty space is shaped by placing at least one of a balloon with air or fluid, or any other filler material that will not influence load transfer effects between the inner and outer tubes prior to the filling.

2. The method according to claim 1, wherein the inner and outer tubes are flanged to each other so as to create a chamber between the outer surface of the inner tube and the inner surface of the outer tube, said chamber between the inner and outer tubes being filled with the cement layer, and
   wherein the empty space in the cement layer along the circumferential direction corresponds to cementing failures in the inner tube.

3. The method according to claim 2, wherein the empty space is fitted with a first access means through the inner tube,
   and pressure is applied to the inner tube through the first access means by using an air compressor or a pump.

4. The method according to claim 2, wherein the outer tube has a circular cross-section.

5. The method according to claim 2, wherein the outer tube has an oval cross-section.

6. The method according to claim 2, wherein the empty space is disposed concentrically around a segment of the inner tube.

7. The method according to claim 2, wherein the empty space is disposed in segments symmetrically distributed along the circumferential direction.

8. The method according to claim 2, wherein the empty space is disposed in segments asymmetrically distributed along the circumferential direction.

9. The method according to claim 2, wherein the outer tube is made with a metallic material, and
wherein the empty space is fitted with a welded piece of rolled sheet configured to provide a structural support.

10. The method according to claim 1, wherein the test body is fitted with semi-spherical flanges at both ends along an axial direction of the test body,
the both ends of the test body are fitted with a second access means, and pressure is applied inside the inner tube through the second access means using an air compressor or a pump.

11. The method according to claim 1, wherein the outer tube is made with a metal material configured to support the cement layer of the test body.

12. The method according to claim 1, wherein the inner tube is centered with respect to the outer tube.

13. The method according to claim 1, wherein the inner tube is not centered with respect to the outer tube.

14. The method according to claim 1, wherein the step of applying uniform stresses on test body having the empty space along the circumferential direction simulates the non-uniform loads corresponding to at least one of cementing failures, presence of stress anisotropy in a borehole and irregular geometry.

15. The method according to claim 1, wherein the any other filler material is selected from the group consisting of a polyurethane foam, a polyethylene foam, a polystyrene foam, a wood frame, and a bamboo frame.

16. The method according to claim 1, wherein the empty space continuously extends with a length of at least 5% of a total circumference of the inner tube.

17. The method according to claim 1, wherein the empty space includes two separate empty spaces, each continuously extending with a length of at least 25% of a total circumference of the inner tube.

* * * * *